(12) United States Patent
Luzzatto et al.

(10) Patent No.: US 7,942,265 B2
(45) Date of Patent: May 17, 2011

(54) PACKAGING SYSTEM FOR ABSORBENT PAD DISPOSING UNITS

(76) Inventors: Michal Luzzatto, Omer (IL); Zeev Jelinek, Beer Sheva (IL)

( * ) Notice: Subject to any disclaimer, the term of this patent is extended or adjusted under 35 U.S.C. 154(b) by 113 days.

(21) Appl. No.: 12/302,103

(22) PCT Filed: May 28, 2007

(86) PCT No.: PCT/IL2007/000641
§ 371 (c)(1), (2), (4) Date: Jan. 12, 2009

(87) PCT Pub. No.: WO2007/138581
PCT Pub. Date: Dec. 6, 2007

(65) Prior Publication Data
US 2011/0036737 A1 Feb. 17, 2011

(30) Foreign Application Priority Data
May 31, 2006 (IL) .......................... 176080

(51) Int. Cl.
*A61B 17/06* (2006.01)
(52) U.S. Cl. ...................................... 206/440
(58) Field of Classification Search .................. 206/440, 206/441, 494, 561, 812, 823; 604/358, 385.02
See application file for complete search history.

(56) References Cited

U.S. PATENT DOCUMENTS

| | | | |
|---|---|---|---|
| 2,750,033 A * | 6/1956 | Pickens | 206/440 |
| 4,857,066 A * | 8/1989 | Allison | 604/385.13 |
| 6,267,232 B1 | 7/2001 | LeJeune | |
| 6,685,020 B2 | 2/2004 | Briseboi et al. | |
| 2003/0089633 A1* | 5/2003 | Sorebo et al. | 206/440 |
| 2005/0085781 A1* | 4/2005 | Corlett | 604/385.02 |
| 2005/0098466 A1* | 5/2005 | Thomas | 206/440 |
| 2005/0209576 A1* | 9/2005 | Hirotsu | 604/385.02 |
| 2006/0058770 A1* | 3/2006 | Bohlen et al. | 604/385.02 |

OTHER PUBLICATIONS

PCT/IL07/00641 Search Report dated Jun. 18, 2008.

* cited by examiner

*Primary Examiner* — Luan K Bui
(74) *Attorney, Agent, or Firm* — Roach, Brown, McCarthy & Gruber P.C.; Kevin D. McCarthy

(57) ABSTRACT

A packaging system for absorbent pad disposing units that comprises a receptacle and a plurality of absorbent pad disposing units contained within the receptacle. Each of the absorbent pad disposing units comprises a sterile absorbent pad and a dedicated refuse bag in a compressed state which is in cooperation with the absorbent pad. Each of the absorbent pad disposing units can be removed from the receptacle upon demand. The dedicated refuse bag is separable from the corresponding absorbent pad. A spent absorbent pad is can be disposed within the refuse bag when the refuse bag is in an expanded state.

10 Claims, 4 Drawing Sheets

PACKAGING SYSTEM FOR ABSORBENT PAD DISPOSING UNITS

CLAIM OF PRIORITY

This application claims priority as a 371 of international of PCT/IL2007/000641, filed on May 28, 2007; which claims priority to Israeli patent application number 176080, filed on May 31, 2006.

FIELD OF THE INVENTION

The present invention relates to the field of hygienic articles. More particularly, the invention relates to a packaging system for absorbent pad disposing units.

BACKGROUND OF THE INVENTION

Those that dispose of absorbent pads, such as bandages or tampons, tend to cover the pads with tissue or the like, due to their unaesthetic appearance. It would be desirable to provide a packaging system that provides both a new absorbent pad and a dedicated bag in which a spent absorbent bag is to be disposed.

It is an object of the present invention to provide a packaging system that dispenses both a new absorbent pad and a dedicated bag in which a spent absorbent pad is to be disposed.

It is another object of the present invention to provide an absorbent pad disposing unit that is compactly stored.

Other objects and advantages of the invention will become apparent as the description proceeds.

SUMMARY OF THE INVENTION

The present invention provides a packaging system for absorbent pad disposing units, comprising a receptacle and a plurality of absorbent pad disposing units contained within said receptacle, wherein each of said absorbent pad disposing units comprises a sterile absorbent pad and a dedicated refuse bag in a compressed state which is in cooperation with said absorbent pad, each of said absorbent pad disposing units being removable from said receptacle on demand.

As referred to herein, an "absorbent pad" is an element made from absorbent material of any desired shape, color, and configuration, such as tampons, sanitary napkins, panty liners, bandages, and gauze, suitable to absorb body discharges or exudates.

The refuse bag, which is preferably opaque and, is separable from the absorbent pad, and a spent absorbent pad can suitably be disposed within the refuse bag when in an expanded state.

The refuse bag is preferably made of an essentially water-impermeable material, e.g., a plastic material or a material that comprises a plastic material.

Preferably, the refuse bag has an integral closure device in the vicinity of the opening thereof (hereinafter referred to also as "mouth".)

The absorbent pad disposing units are preferably arranged in the receptacle such that they are in a standing position. The disposing units may be in abutting positioned relationship with one another or may be inserted in individual chambers defined by a plurality of mutually parallel first partition elements and a plurality of mutually parallel second partition elements, wherein the second partition elements are perpendicularly connected to the first partition elements. The area of each chamber is sized to be substantially equal to, and slightly greater than, an absorbent pad disposing unit.

In one aspect, the dedicated refuse bag is sized such that it can be wrapped about slightly less than the entire circumference of a cylindrical absorbent pad, completely wrapped thereabout, or wrapped more than once thereabout.

In one aspect, the absorbent pad disposing unit further comprises a protective layer enclosing the absorbent pad, the dedicated refuse bag being releasably attached to, or wrapped about, said protective layer. The refuse bag may be attached to the protective layer by means of a perforated strip.

DETAILED DESCRIPTION OF PREFERRED EMBODIMENTS

Figure 1:
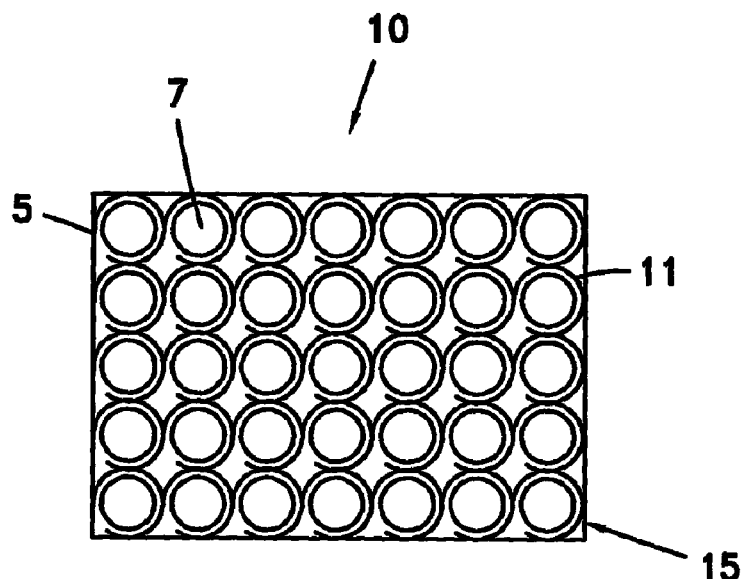
FIG. 1 is a schematic plan view of a packaging system, according to one preferred embodiment of the invention.

FIG. 1 schematically illustrates a packaging system according to a preferred embodiment of the present invention, and is generally indicated by numeral 10. Packaging system 10 is provided with receptacle 5, which is made of any convenient material such as plastic or cardboard and is of any convenient shape, e.g. rectangular as shown. A plurality of absorbent pad disposing units 15 are stored within receptacle 5. Each absorbent pad disposing unit 15 comprises a sterile absorbent pad 7, e.g. of circular cross-section as shown, and a dedicated refuse bag 11, wrapped around the corresponding absorbent pad 7 when in a compressed state. Refuse bag 11 may be partially wrapped around the corresponding absorbent pad 7, or may be wrapped once, twice, or any other convenient number of times about the corresponding absorbent pad 7.

The plurality of absorbent pad disposing units 15 are arranged such that when a maximum number of absorbent pad disposing units 15 are contained within receptacle 5, each absorbent pad disposing unit 15 is in abutting positioned relationship with adjacent absorbent pad disposing units and is thereby urged to a standing position. A "standing position", as referred to herein, is a position that facilitates optimal use of an absorbent pad disposing unit 15. In the illustrated packaging system, the standing position is achieved when the axis of each cylindrical absorbent pad 7 is mutually parallel and the dedicated refuse bag 11 remains wrapped around absorbent pad 7. Accordingly, when an absorbent pad disposing unit 15 is removed from receptacle 5 upon demand, refuse bag 11 remains in cooperation with absorbent pad 7.

Figure 2:
FIG. 2 is a side view of a refuse bag in a compressed state, according to a preferred embodiment of the invention.
Figure 3:
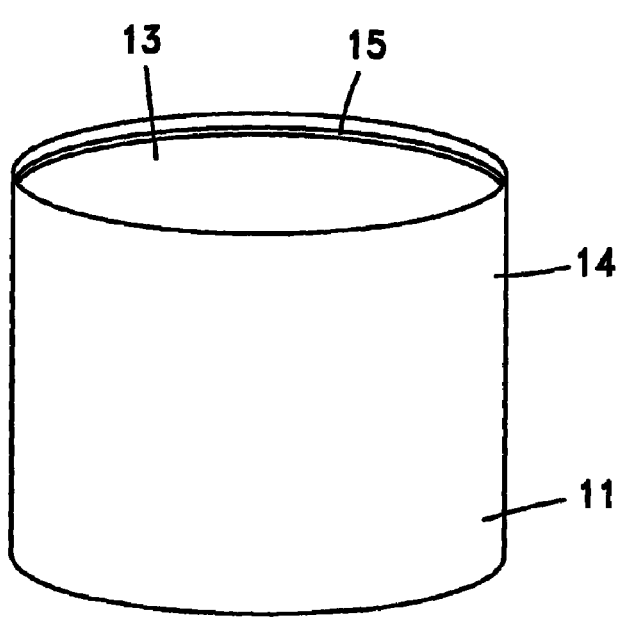
FIG. 3 is a perspective view of the refuse bag of FIG. 2 in an expanded state, showing one bag closure device.

FIG. 2 illustrates a refuse bag 11, which can be made of any suitable plastic material, e.g., an elastic material, when in a compressed state, after being separated from an absorbent pad. After being used and soiled, the absorbent pad, particularly a female hygienic absorbent pad, needs to be disposed due to its unsightly appearance. Since the disposing unit advantageously provides a dedicated refuse bag 11, the latter may be expanded, as shown in FIG. 3, and the soiled absorbent pad may be disposed within interior 13 thereof. Refuse bag 11, which is preferably opaque to conceal the soiled absorbent pad, may be closed by affixing together two or more portions, e.g. strips, of adhesive material 15 applied to the interior of bag upper end 14.

Figure 4:
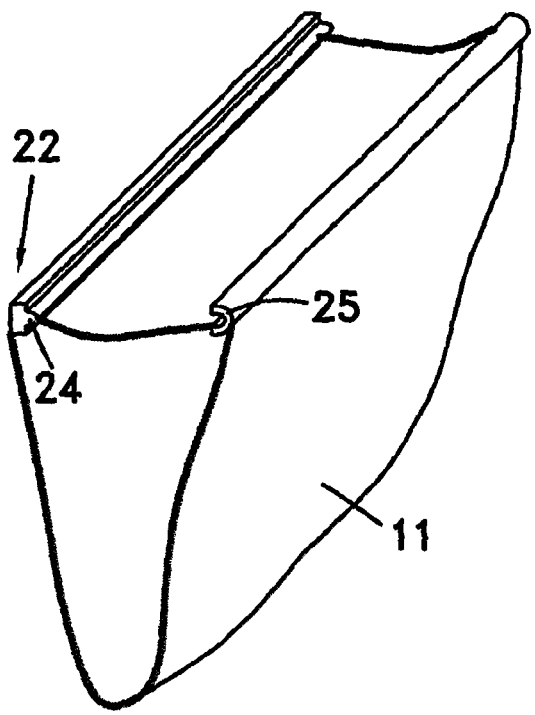
FIGS. 4-6 each schematically illustrates other configurations of a bag closure device, according to alternative preferred embodiments of the invention.
Figure 5:
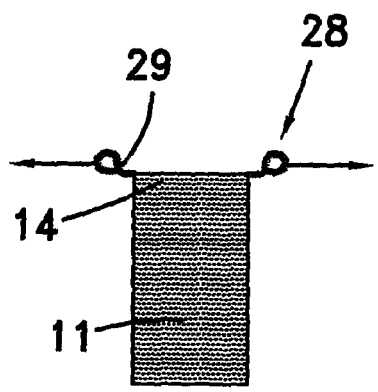
Figure 6:
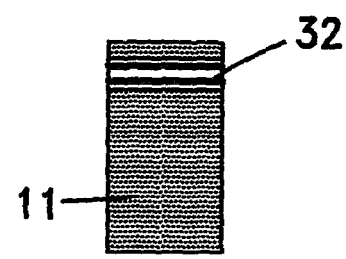

Refuse bag 11 may be closed by any other suitable closure or sealing means, well known to those skilled in the art, such as the snap closure 22 illustrated in FIG. 4 which comprises a male element 24 and a complementary female element 25 that are adapted to snap together, or the tie closure 28 illustrated in FIG. 5 provided with a cord element 29 integrally formed with bag upper end 14, which, when pulled, constricts the mouth of the refuse bag, or the ziplock seal 32 illustrated in FIG. 6, having a pair of complementary resilient extruded plastic seal strips with a separable interlockable profile, to facilitate the transfer of refuse bag 11 to a refuse disposal facility, e.g. a public refuse receptacle.

Figure 7:
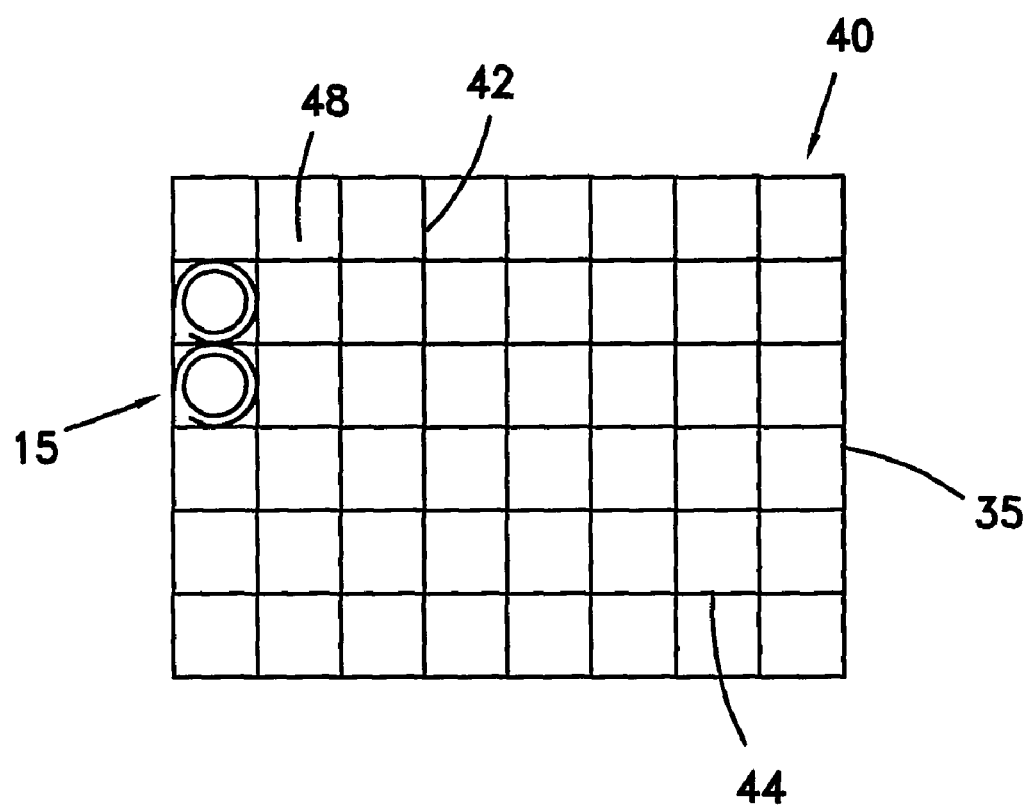
FIG. 7 is a schematic plan view of another preferred embodiment of a packaging system.

FIG. 7 schematically illustrates another preferred embodiment of a packaging system, and is generally indicated by numeral 40. In packaging system 40, receptacle 35 is provided with a plurality of mutually parallel first partition elements 42 and a plurality of mutually parallel second partition elements 44, wherein the second partition elements 44 are perpendicularly connected to first partition elements 42 to define a plurality of essentially rectangular chambers 48. The area of each chamber 48, enclosed by two first partition elements 42 and two second partition elements 44, is sized to be substantially equal to, and slightly greater than, an absorbent pad disposing unit 15, so that an absorbent pad disposing unit 15 inserted within a chamber 48 will be retained in a standing position even though a disposing unit has been removed from all chambers adjacent thereto.

Figure 8:
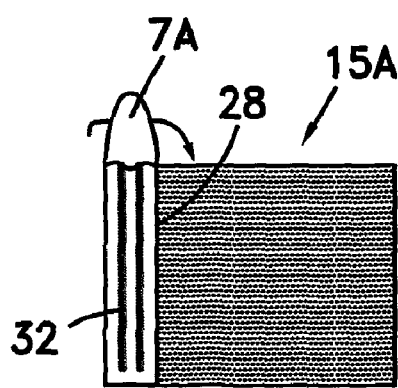
FIG. 8 is a side view of a preferred embodiment of an absorbent pad disposing unit, illustrating the attachment means between the refuse bag and the protective layer of the absorbent pad.

FIG. 8 illustrates a side view of an absorbent pad disposing unit 15A, according to a preferred embodiment of the invention. In disposing unit 15A, the absorbent pad 7A, e.g. a tampon, having a cylindrical base and a conical top portion, is enclosed by a protective layer 32, which is only partially shown in the figure. Refuse bag 11 is attached to protective layer 32 in the vicinity of the cylindrical base by means of perforated strip 28, or by any other convenient detachable attachment means.

Figure 9:
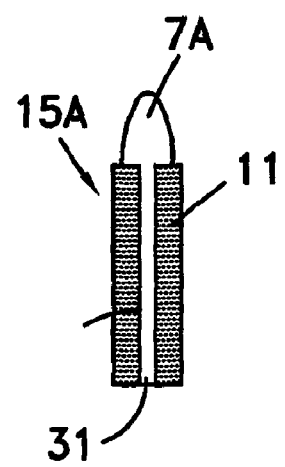
FIG. 9 is a side view of the disposing unit of FIG. 8 with the refuse bag partially wrapped about the absorbent pad.

FIG. 9 illustrates disposing unit 15A as refuse bag 11 is partially wrapped about absorbent pad 7A. Refuse bag 11 in a compressed state is sized such that it can be wrapped slightly less than the entire circumference of cylindrical base 31.

Figure 10:
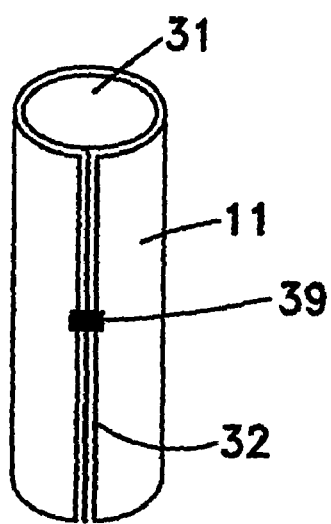
FIG. 10 is a rear perspective view of a disposing unit, according to a preferred embodiment of the invention, wherein the refuse bag is completely wrapped around a cylindrical absorbent pad, illustrating an affixing means by which the lateral ends of the refuse bag are releasably attached together.

Similarly, refuse bag 11 may be sized to be completely wrapped around the circumference of cylindrical base 31, or to be wrapped more than once around the circumference of cylindrical base 31. In FIG. 10, refuse bag 11 is shown to be completely wrapped around the circumference of cylindrical base 31, and lateral ends 32 of refuse bag 11 are releasably attached together with a suitable affixing means 39, such as pressure sensitive adhesive.

Figure 11:
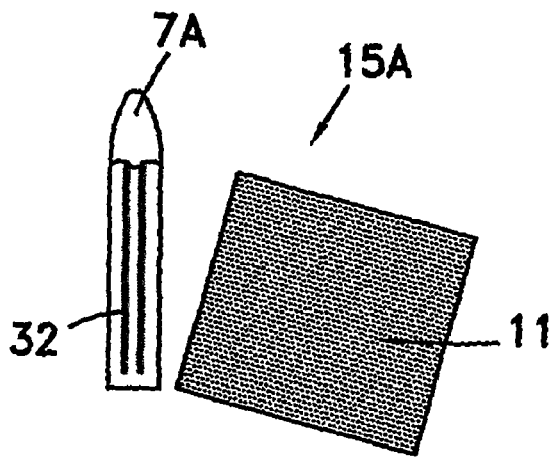
FIG. 11 is a side view of a refuse bag, according to a preferred embodiment of the invention, being separated from the protective layer of an absorbent pad.
Figure 12:
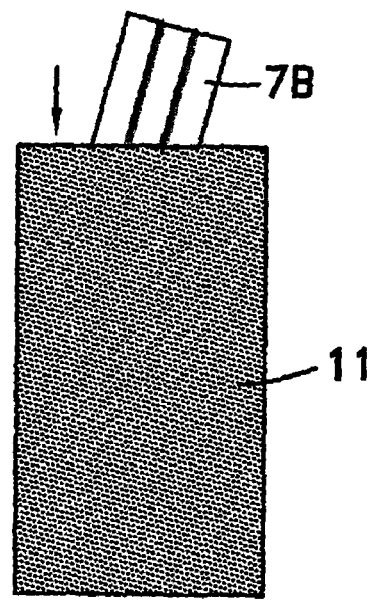
FIG. 12 is a side view of a spent absorbent pad which is disposed within a refuse bag in an expanded state.

After refuse bag 11 in a compressed state is separated from protective layer 32 of absorbent pad 7A as shown in FIG. 11, protective layer 32 is peeled off from absorbent pad 7A, to allow the latter to be used to absorb, body discharges or exudates. After refuse bag 11 is expanded as shown in FIG. 12, the soiled absorbent pad 7B is inserted into the interior thereof.

The absorbent pads may be of any other convenient configuration, whether curvilinear as shown, planar such as when bandages or gauze is employed, or any other desired shape. The refuse bag may assume any convenient configuration to conform to that of the absorbent pad. The standing position of the disposing units in the selected packaging system may be such that the disposing units are stacked one on top of the other, such that they are in abutting positioned relationship, or arranged in any other suitable arrangement. When a standing position of the absorbent pad disposing units is used, their accessibility to users is increased, thereby increasing their utility for hygienic, high-volume applications. An exemplary environment for the packaging system of the present invention is a public bathroom facility for the benefit of female users, or a hospital wherein wound dressings, for example, are replaced on a regular basis and there is a need to dispose a soiled bandage in a dedicated refuse bag, in order to considerably reduce the risk of transmission of infectious diseases.

While some embodiments of the invention have been described by way of illustration, it will be apparent that the invention can be carried out with many modifications, variations and adaptations, and with the use of numerous equivalents or alternative solutions that are within the scope of persons skilled in the art, without departing from the spirit of the invention or exceeding the scope of the claims.

The invention claimed is:

1. A packaging system for absorbent pad disposing units, comprising a receptacle and a plurality of absorbent pad disposing units contained within said receptacle, each of said absorbent pad disposing units being removable from said receptacle upon demand wherein each of said absorbent pad disposing units comprises a sterile absorbent pad and a dedicated refuse bag in a compressed state which is in cooperation with said absorbent pad, wherein said absorbent pad disposing unit further comprises a protective layer enclosing said absorbent pad, said dedicated refuse bag being releasably attached to said protective layer by means of a perforated strip, wherein said dedicated refuse bag is separable from the corresponding absorbent pad, wherein a spent absorbent pad is capable of being disposed within the dedicated refuse bag when said refuse bag is in an expanded and separated state.

2. The packaging system according to claim 1, wherein the refuse bag has an integral closure device in the vicinity of its opening or mouth.

3. The packaging system according to claim 1, wherein the refuse bag is opaque.

4. The packaging system according to claim 1, wherein the refuse bag is made of an essentially water-impermeable material.

5. The packaging system according to claim 4, wherein the essentially water-impermeable material comprises a plastic material.

6. The packaging system according to claim 1, wherein the absorbent pad disposing units are arranged in the receptacle such that they are in a standing position.

7. The packaging system according to claim 6, wherein the disposing units are in abutting positioned relationship with one another within the receptacle thereby to assume a standing position.

8. The packaging system according to claim 1, wherein the disposing units are inserted in individual chambers defined by a plurality of mutually parallel first partition elements and a plurality of mutually parallel second partition elements such that said second partition elements are perpendicularly connected to said first partition elements.

9. The packaging system according to claim 8, wherein the area of each chamber is sized to be substantially equal to, and slightly greater than, that of an absorbent pad disposing unit.

10. The packaging system according to claim 1, wherein the dedicated refuse bag is sized such that it is wrapped about slightly less than the entire circumference of a cylindrical absorbent pad, completely wrapped thereabout, or wrapped more than once thereabout.

* * * * *